(12) United States Patent
Gable

(10) Patent No.: US 12,296,225 B2
(45) Date of Patent: May 13, 2025

(54) SYSTEM AND METHOD FOR MEASURING FORCE AND REPETITIVE MOTION FOR THERAPEUTIC AND FITNESS GOALS

(71) Applicant: Derek J Gable, Rancho Palos Verdes, CA (US)

(72) Inventor: Derek J Gable, Rancho Palos Verdes, CA (US)

( * ) Notice: Subject to any disclaimer, the term of this patent is extended or adjusted under 35 U.S.C. 154(b) by 307 days.

(21) Appl. No.: 17/966,136

(22) Filed: Oct. 14, 2022

(65) Prior Publication Data
US 2023/0031692 A1 Feb. 2, 2023

Related U.S. Application Data

(63) Continuation-in-part of application No. 17/210,900, filed on Mar. 24, 2021, now abandoned.

(51) Int. Cl.
*A63B 24/00* (2006.01)
*A63B 21/008* (2006.01)

(52) U.S. Cl.
CPC ...... *A63B 24/0003* (2013.01); *A63B 21/0083* (2013.01); *A63B 24/0062* (2013.01); *A63B 2220/51* (2013.01); *A63B 2225/20* (2013.01)

(58) Field of Classification Search
CPC ............ A63B 24/0062; A63B 21/0552; A63B 71/0622; A63B 2071/065; A63B 2071/0658; A63B 2220/17; A63B 2220/51; A63B 2220/833; A63B 2225/20; A63B 2225/50; A63B 21/00178; G16H 20/30; G16H 40/67
See application file for complete search history.

(56) References Cited

U.S. PATENT DOCUMENTS

| | | | | |
|---|---|---|---|---|
| 2008/0119763 | A1* | 5/2008 | Wiener | A61B 5/224 600/587 |
| 2012/0329615 | A1* | 12/2012 | Jeong | G16H 40/63 482/113 |
| 2014/0342878 | A1* | 11/2014 | Hashish | A63B 21/045 482/8 |
| 2017/0246507 | A1* | 8/2017 | Kennington | A63B 21/0087 |
| 2020/0139187 | A1* | 5/2020 | Kennington | A63B 71/0622 |

* cited by examiner

*Primary Examiner* — Francis C Gray
(74) *Attorney, Agent, or Firm* — Landmark Intellectual Property Law, LLC; Gregory M Murphy

(57) ABSTRACT

The invention is directed to systems, devices, and methods for measuring force and repetitions during exercise or rehabilitation activities. Devices in accordance with embodiments may include: a casing; a processor within the casing; a display visibly on the casing; a first attachment portion on one end of the casing; a second attachment portion on an opposite end of the casing; and a force sensor connected to the first and the second attachment portion, the force sensor in communication with the processor. Methods may include: attaching a pneumatic exercise device to the wireless force measurement device; conducting exercises causing a piston in the pneumatic exercise device to move compared to from the wireless force measurement device; counting, by the device, the number of times the piston moves towards or away from the device; determining, by the device the amount of force applied through the pneumatic exercise device during the exercise.

12 Claims, 10 Drawing Sheets

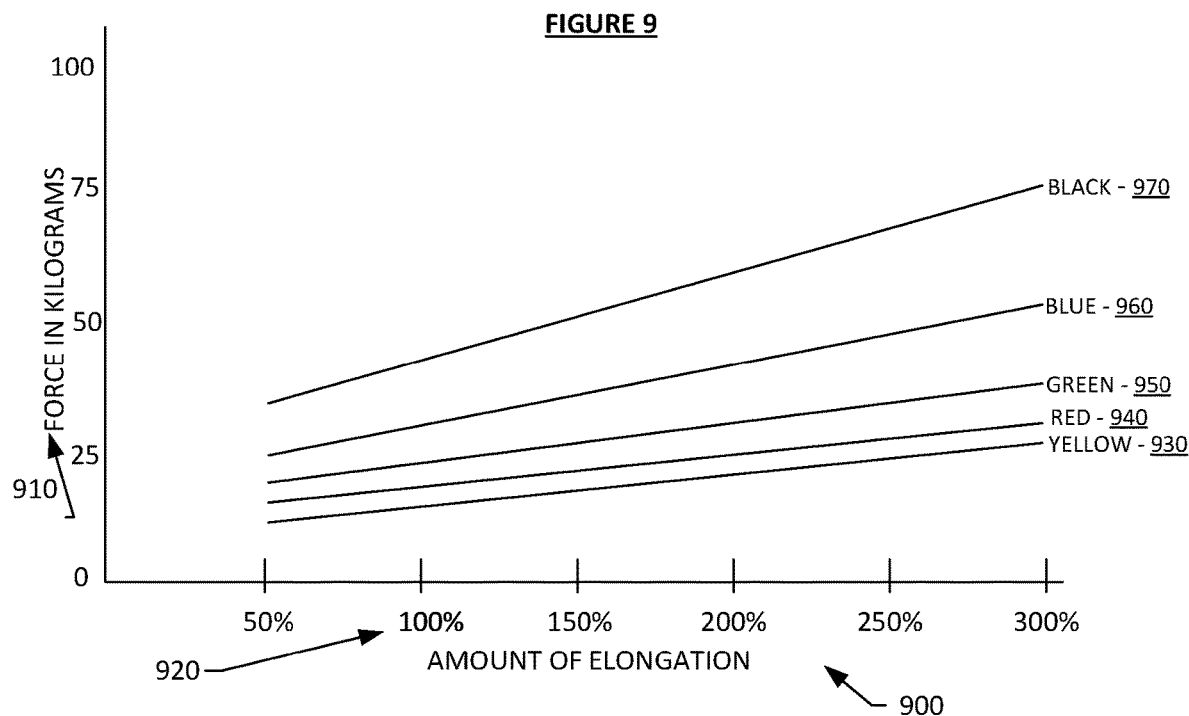
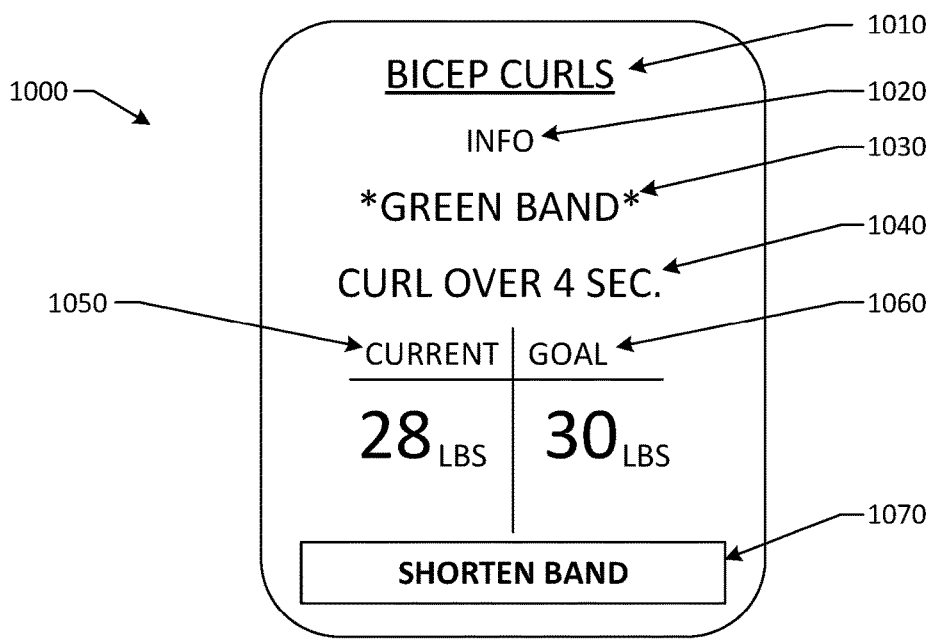

SYSTEM AND METHOD FOR MEASURING FORCE AND REPETITIVE MOTION FOR THERAPEUTIC AND FITNESS GOALS

RELATED APPLICATIONS

This application is a continuation-in-part of, and claims priority to, U.S. patent application Ser. No. 17/210,900, entitled "System and Method for Measuring Force and Repetitive Motion for Therapeutic and Fitness Goals," filed on 24 Mar. 2021, which is incorporated by reference herein in its entirety.

BACKGROUND

In general, the present invention is directed to a device for tracking usage and progress of physical activity, and/or flexibility. More specifically, the present invention is directed to a communicative force sensor that can be configured to record repetitive activity, conditioning, strength progress, stretching abilities, and the like, and report or communicate such information to a user device or a device of a health care provider.

Often following in the recovery of an injury or surgical event, a patient may be advised and/or required to perform certain physically therapeutic activities. Regular and consistent activities, often coupled with increasing loads or resistance, may be necessary or highly desirable for a quick, full, and successfully recovery.

However, what is prescribed or advised for a patient is not always performed. Oftentimes, although a patient has been advised that such activity may be highly beneficial to recovery, the patient may not undertake or honestly report his or her activities.

From a healthcare provider's perspective, patient compliance and recovery may directly or indirectly impact professional liability insurance rate, coverage, quality controls, or other metrics that may be tracked and/or recorded.

From a different perspective, exercise resistance bands are often used in lieu of, or in addition to, traditional free-weights or other machines. However, while resistance bands come in categories of resistance, the actual degree of force required to stretch the band is generally related to the amount of elongation of the band. For example, stretching a particular band only 10% may require force X, while stretching the band 250% may require three times the force, or force 3(x). Therefore, it is often difficult while using resistance bands to have a clear understanding of the amount of work the body is expending. It is therefore difficult to properly track progress and/or plan an incremental workout regimen using resistance bands.

In addition to resistance bands, additional devices may be used. For example, a user may utilize a pneumatic cylinder device that may use compression and release of air to cause resistance. However, as with resistance bands, it may be difficult to accurately estimate, determine, or track an actual amount of force exerted by the user.

Accordingly, it is desirable to provide systems and methods of tracking user repetitions, efforts, and abilities, with greater detail and measured force. It is also desirable to provide systems and methods that may permit direct or indirect communication with a medical care professional in order to show and/or substantiate claims of use (such as in a physical therapy embodiment).

SUMMARY OF THE INVENTION

In accordance with some embodiments of the present invention, aspects may include: a device for measuring force and repetitions during exercise or rehabilitation activities, the device comprising: a casing; a processor disposed within the casing; a display visibly disposed on the casing and communicatively connected to the processor; a first attachment portion on one end of the casing; a second attachment portion on an opposite end of the casing from the first attachment portion; and a force sensor disposed within the casing and connected to the first attachment portion and the second attachment portion, the force sensor in communication with the processor.

In accordance with some embodiments of the present invention, aspects may include: a device for measuring force and repetitions during exercise or rehabilitation activities, the device comprising: a first attachment portion on one end of a casing; a second attachment portion on an opposite end of the casing from the first attachment portion; and the casing, holding: a processor; a force sensor connected to the first attachment portion and the second attachment portion, the force sensor in communication with the processor; a memory module, configured to store past information related to repetitions, force levels, and time and day; a communication module, connected to the processor and configured to provide wireless communication; and a display visibly disposed on the casing and communicatively connected to the processor.

In accordance with some embodiments of the present invention, aspects may include: a method for measuring force and repetitions during exercise or rehabilitation activities, using a wireless force measurement device, the method comprising: attaching an exercise band, pneumatic device, or other equipment to the wireless force measurement device; conducting exercises causing the exercise band to stretch and pull away from the wireless force measurement device; counting, by the wireless force measurement device, the number of times the band stretches and pulls away or pneumatic cylinder compresses or elongates from the wireless force measurement device; determining, by the wireless force measurement device the amount of force applied through the exercise band during the exercise.

These and other aspects will become apparent from the following description of the invention taken in conjunction with the following drawings, although variations and modifications may be affected without departing from the spirit and scope of the novel concepts of the invention.

DESCRIPTION OF THE FIGURES

The present invention can be more fully understood by reading the following detailed description together with the accompanying drawings, in which like reference indicators are used to designate like elements. The accompanying figures depict certain illustrative embodiments and may aid in understanding the following detailed description. Before any embodiment of the invention is explained in detail, it is to be understood that the invention is not limited in its application to the details of construction and the arrangements of components set forth in the following description or illustrated in the drawings. The embodiments depicted are to be understood as exemplary and in no way limiting of the overall scope of the invention. Also, it is to be understood that the phraseology and terminology used herein is for the purpose of description and should not be regarded as limiting. The detailed description will refer to the following figures, in which:

FIG. 9 illustrates a force graph associated with the use of exercise resistance bands, in accordance with some embodiments of the preset invention.

FIG. 10 depicts an exemplary display of a device for measuring force and/or repetitive motions, in accordance with some embodiments of the present invention.

Figure 1:
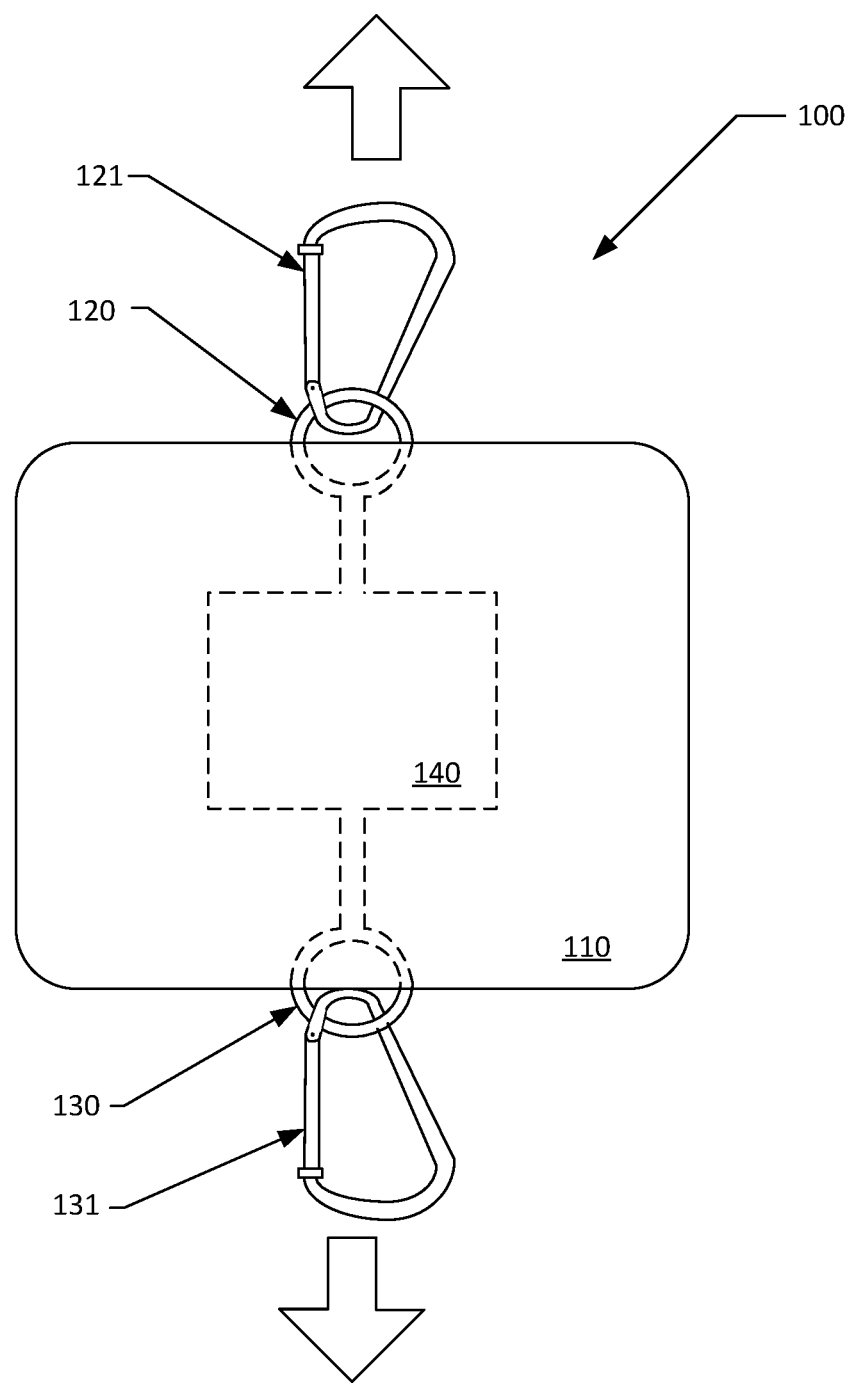
FIG. 1 illustrates an exemplary device for measuring force and/or repetitive motions, in accordance with some embodiments of the present invention.

Before any embodiment of the invention is explained in detail, it is to be understood that the present invention is not limited in its application to the details of construction and the arrangements of components set forth in the following description or illustrated in the drawings. The present invention is capable of other embodiments and of being practiced or being carried out in various ways. Also, it is to be understood that the phraseology and terminology used herein is for the purpose of description and should not be regarded as limiting.

DETAILED DESCRIPTION

The matters exemplified in this description are provided to assist in a comprehensive understanding of various exemplary embodiments disclosed with reference to the accompanying figures. Accordingly, those of ordinary skill in the art will recognize that various changes and modifications of the exemplary embodiments described herein can be made without departing from the spirit and scope of the claimed invention. Descriptions of well-known functions and constructions are omitted for clarity and conciseness. Moreover, as used herein, the singular may be interpreted in the plural, and alternately, any term in the plural may be interpreted to be in the singular.

As noted above, during recovery following injury or a surgical event, medical professionals may assign, require, or request that a patient perform various repetitive activities to increase strength, flexibility, promote blood flow, and/or prevent muscle wasting or atrophy. However, it may be difficult to track progress, which often necessitates or makes desirable frequent doctor or physical therapy visits. As many patients recovering from such circumstances are less than fully ambulatory, such requirements may increase stress or difficulty on the patient. The inconvenience of frequent visits, coupled with potential pain or discomfort in making such visits, may cause less than complete compliance.

Moreover, even when performing assigned activities at home, it may be difficult to encourage compliance, track, and record progress. In accordance with some embodiments of the present invention, a device may be calibrated to specific activities or specific resistance bands. In accordance with some embodiments of the present invention a healthcare professional may be able to upload specific regiments to the device, or alternatively to a user's phone that may then interact with the device. Communications regarding goals, achievements, progress, difficulties, etc. may be communicated between the device and/or user's phone and the healthcare professional.

Similar to tracking progress for therapeutic use, in accordance with some embodiments of the present invention may be used for fitness and/or muscle growth. Typically, building muscle requires bulky equipment (such as but not limited to free weights, barbells, or various machines). Exercise resistance bands generally provide exercises that may increase muscle growth or toning, but are often difficult to use to judge or track progress. As discussed in greater detail below, the force curve of such resistance bands shows that the applied force on a given band may vary based on the extent of motion (i.e., length or stretch), and at times, the rate of motion.

Pneumatic devices, such as those set forth in FIGS. 11-13 and discussed in greater detail below, may also be used. In the use of such devices, it may again be difficult to properly and accurately measure forces exerted or applied by the user.

Accordingly, it can be difficult to make gains in strength or toning, as there is no clear indication to the user of how much force is used or applied.

In accordance with some embodiments of the present invention—and as discussed in greater detail below—a device may be used to offer various programs based on resistance bands, which may include workout types, bands for use, rate and/or amount of use to achieve goals, and may also track and show user progress.

With reference to FIG. 1, a device 100 in accordance with some embodiments of the present invention will now be disclosed. Device 100 may comprise a casing 110. Inside casing 110 may be a force sensor 140, which may be connected to first connective portion 120 and second connective portion 130. FIG. 1 shows that various attachment devices 121, 131 may be used to attach various resistance bands or pneumatic devices. When used, the force sensor 140 may measure the amount of force applied. Force sensor 140 may comprise any sort of force sensor as known in the art, such as but not limited to a spring scale force gauge, strain gauge, stretch sensor, force transducer, load cells (such as but not limited to bending beam, shear beams, double-ended shear beam, s-types, etc.). When a force is applied pulling first connective portion 120 and second connective portion 130 in different directions, the amount of force may be measured by sensor 140.

Figure 2:
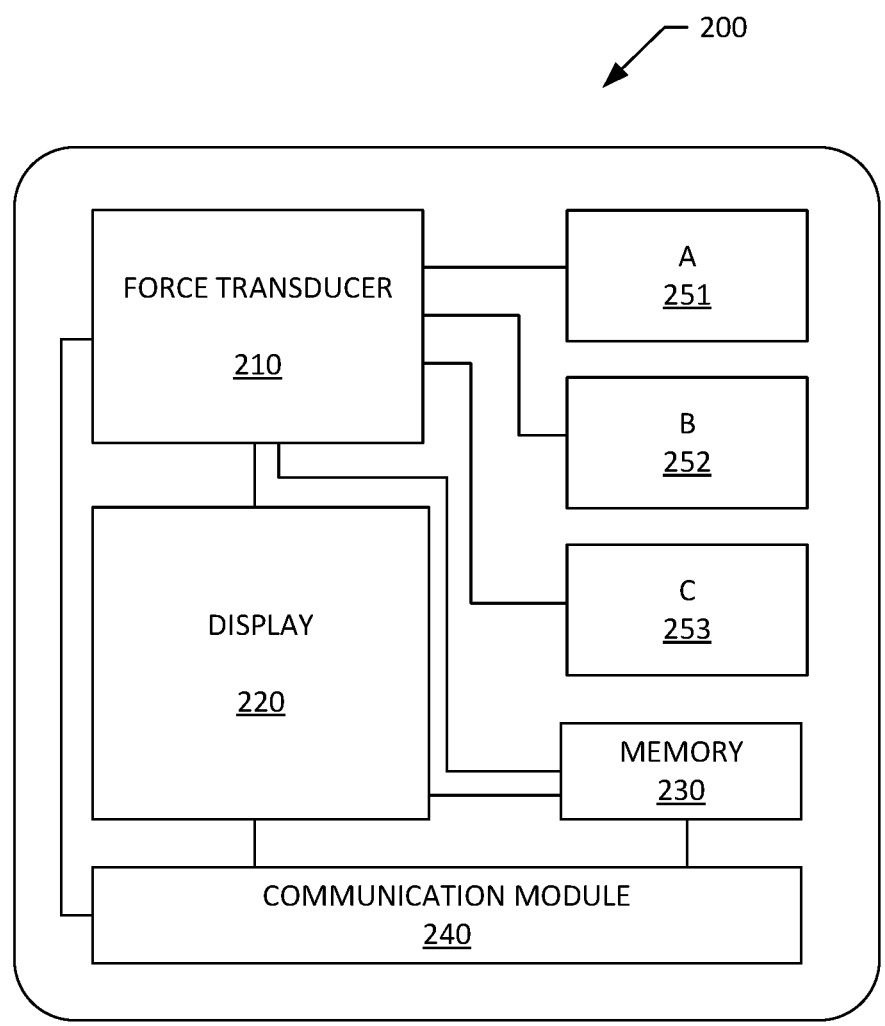
FIG. 2 illustrates an exemplary device for measuring force and/or repetitive motions, in accordance with some embodiments of the present invention.

With reference to FIG. 2, an exemplary device 200 in accordance with some embodiments of the present invention will now be discussed. Device 200 may generally comprise a force sensor 210, a display 220, a memory 230, and a communication module 240. In accordance with some embodiments, device 200 may further comprise selection buttons 250, which may provide options 251, 252, 253.

As discussed above, force sensor 210 may comprise any sort of sensor or element that may measure the amount of force applied to the device. Display 220 may comprise any sort of display (liquid crystal display (LCD), light emitting diodes (LED), plasma display, and/or electroluminescent display (ELD)) that may be used to impart information regarding the force, or number of repetitive motions, or other information associated with the activity, to the user.

Memory 230 may comprise any sort of memory that may be used to record forces measured, number of force repetitions, communications to or from user and/or a healthcare professional, and or other information. Communication module 240 may provide the device 200 with the ability to communicate via forms as known in the art-such as, but not limited to via cellular communications, wireless network communications (e.g., WIFI), near field communications (NFC, such as but not limited to BlueTooth communications), low-power internet of things (IoT) communications, and/or any other type of communications. In accordance with some embodiments of the present invention, communication module 240 may not provide direct communication, but may provide access points and/or ports to enable wired communications, such as USB, mini-USB, HDMI, mini-HDMI, DVI, ethernet, etc.

Selection buttons 250 may provide the user with the ability to select different aspects related to the use of the device 200. For example, in accordance with some embodiments of the present invention, repetitions of activity may be counted. However, compound moves may be miscounted by the device, unless it is indicated to the device that such compound moves are being performed. Accordingly, selection devices 250 may be utilized, in some circumstances, to select different activities. It is contemplated by the present invention that selection buttons 250 may be used to select various items, actions, movements, etc.

Figure 3:
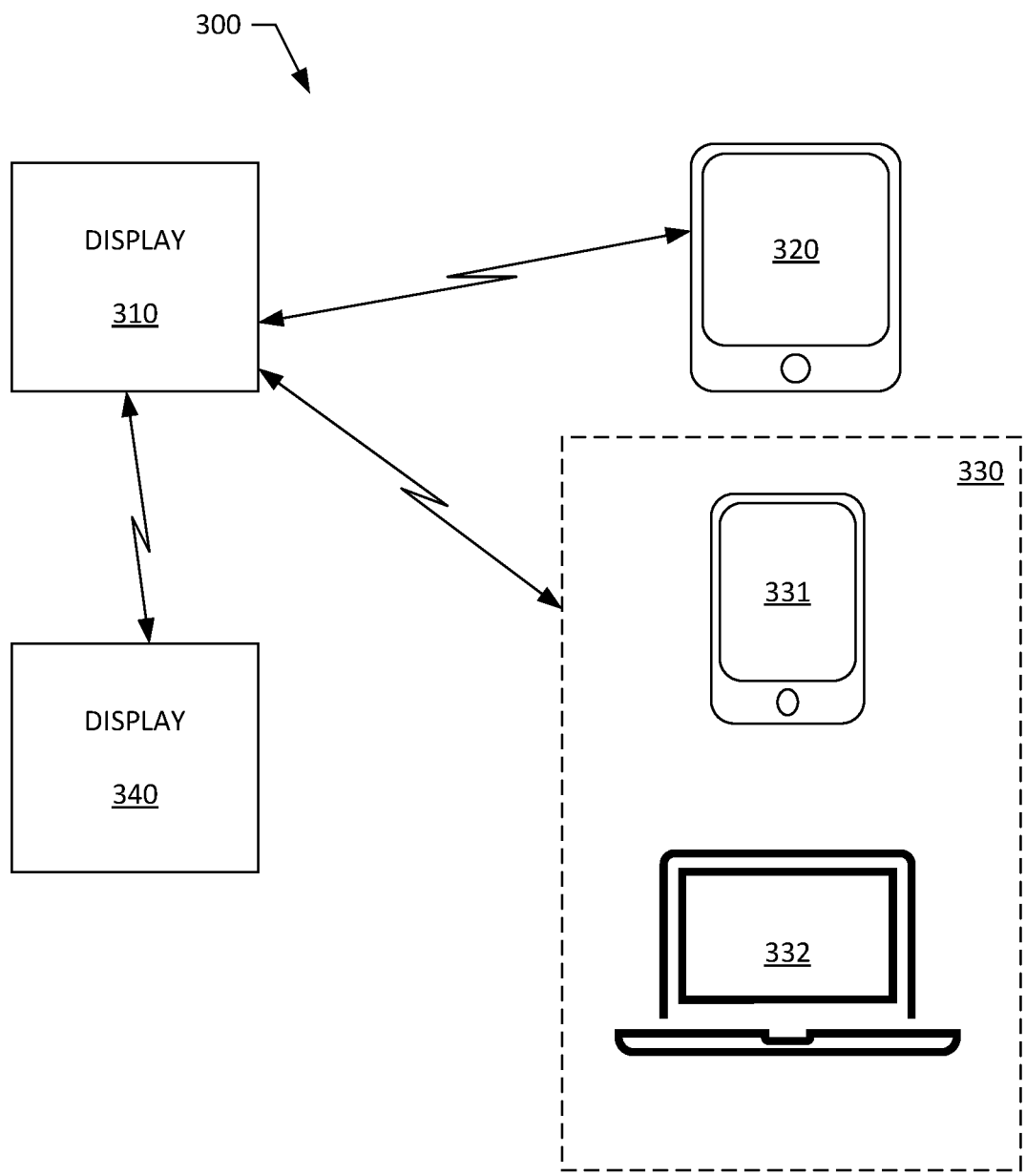
FIG. 3 depicts an exemplary system for measuring force and/or repetitive motions, in accordance with some embodiments of the present invention.

With reference to FIG. 3, a system 300 in accordance with some embodiments of the present invention will now be discussed. System 300 may comprise device 310 which may measure applied forces or repetitive motions. Device 310 may communicate with a user device 320, which may be, for example, a smart phone, computer, tablet, or any other sort of communicative electronic device. Device 310 may also communicate with a health care provider 330, for example by way of a provider's mobile device 331 or computer 332. In this manner, a healthcare professional may both provide goals, exercises, and/or targets to the device, and may be updated as to the activities of the user vis-à-vis the device 310.

In accordance with some embodiments of the present invention, the device may further be in communication with a party 340 unrelated to the immediate treatment of the user. For example, the device may be in communication with a professional liability insurance provider of a healthcare professional associated with the user. The user's compliance with the prescribed activities, for example, may impact a healthcare professional's professional liability insurance, rankings, ratings, and/or other analytics.

Figure 4:
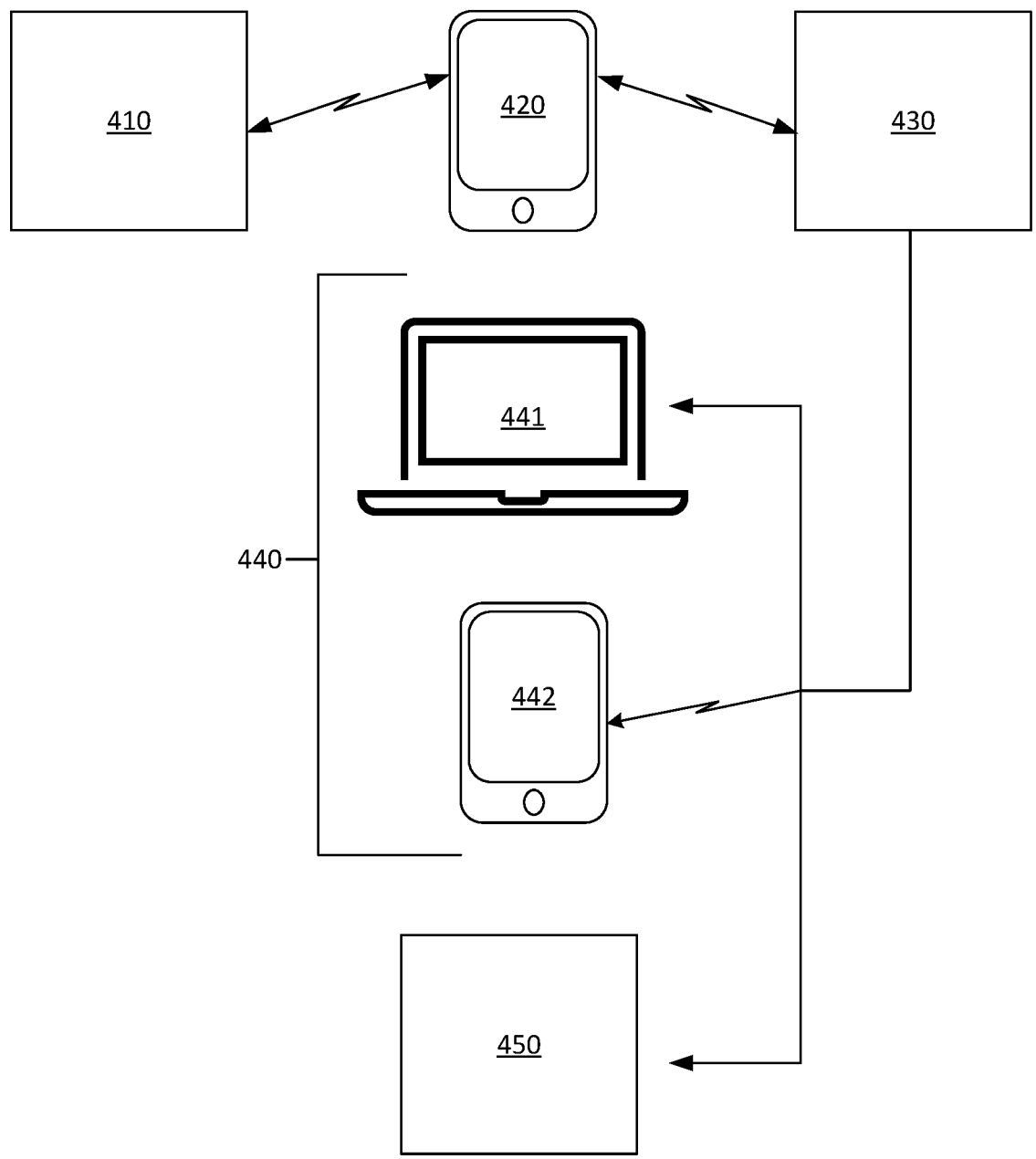
FIG. 4 depicts an exemplary system for measuring force and/or repetitive motions, in accordance with some embodiments of the present invention.

With reference to FIG. 4, a system 400 may now be discussed. Unlike the system shown in FIG. 3, the device 410 in system 400 may not have the ability to communicate directly to healthcare professionals. Rather, the device 410 may communicate, via a user device 420 to a healthcare professional through an application, or "app." Device 410 may then only be equipped with limited communicative attributes, such as near-field communication (NFC) or Bluetooth communication. Device 410 may then communicate with a user device 420, which may comprise a mobile telephone, smart phone, table, computer, etc., which may be in communication with an application that may reside both in part on the user device and in part on a data store 430. Data store 430 may also be in communication with (or accessible by) healthcare professional 440, via a computer 441 or device 442.

In addition, in accordance with some embodiments of the present invention, the device may further be in communication with a party 450 unrelated to the immediate treatment of the user. For example, the device may be in communication with a professional liability insurance provider of a healthcare professional associated with the user. The user's compliance with the prescribed activities, for example, may impact a healthcare professional's professional liability insurance, rankings, ratings, and/or other analytics.

Figure 5:
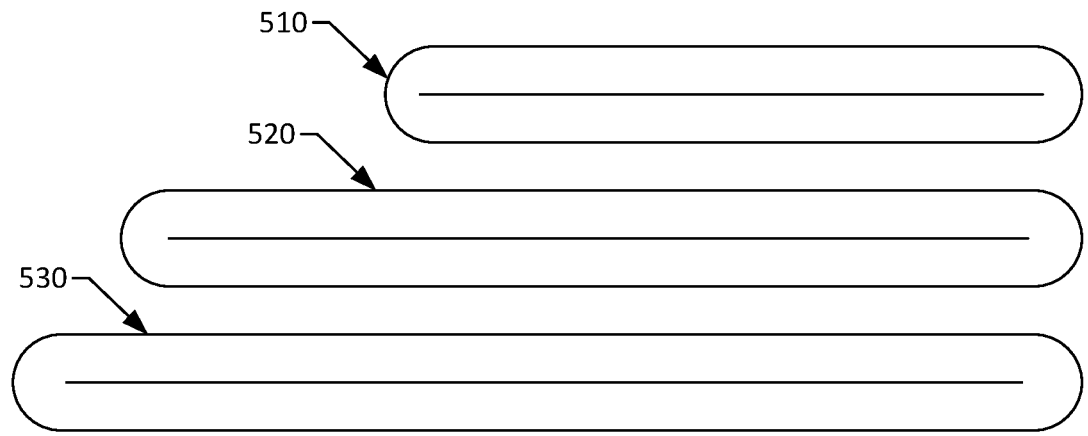
FIG. 5 illustrates exercise resistance bands that may be used with some embodiments of the present invention.

FIG. 5 illustrates several different resistance bands that may be used in accordance with some embodiments of the present invention. Bands 510, 520, 530 may have difficult degrees of resistance, but may each be measured by the device. Alternatively, Bands 510, 520, 530 may have similar degrees of resistance, but may have different lengths. Notably, the present invention can be used with various bands, as it measures the actual force applied, regardless of the band type, color, manufacturer, or even stated strength/weight/force.

Figure 6:
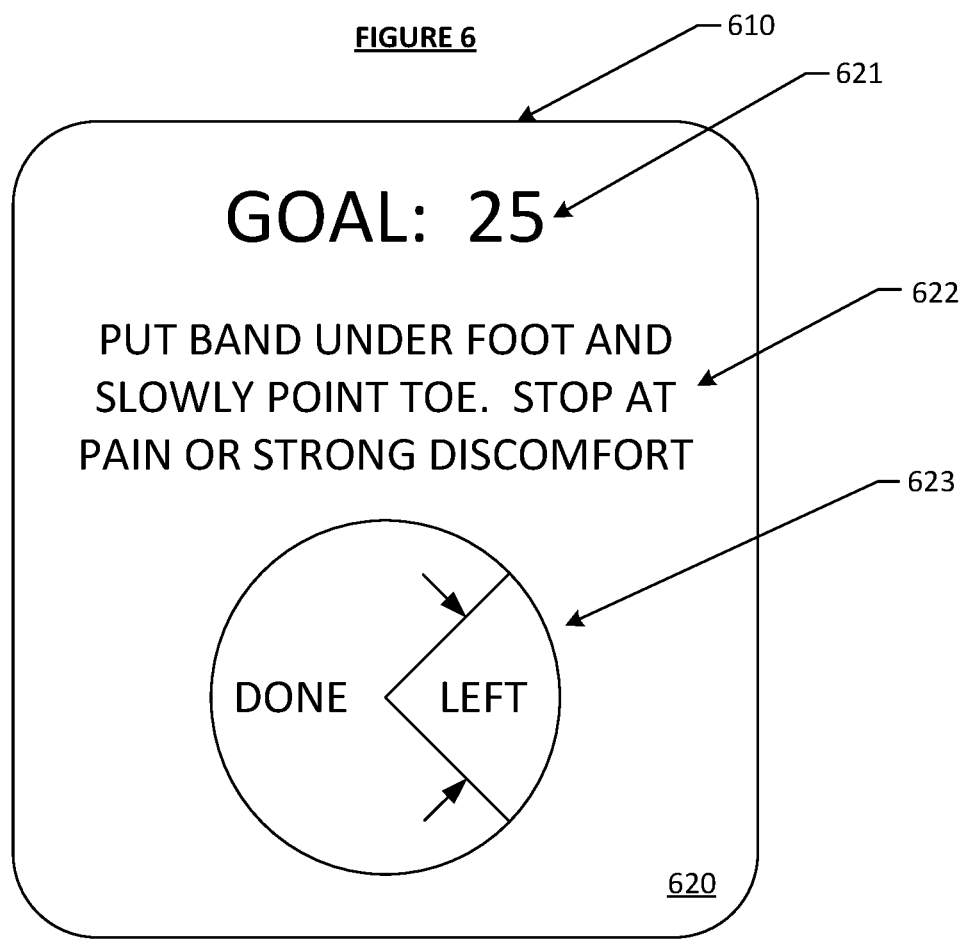
FIG. 6 depicts an illustrative display of an exemplary device for measuring force and/or repetitive motions, in accordance with some embodiments of the present invention.

With reference to FIG. 6, a display 620 of a device 610 in accordance with some embodiments of the present invention will not be discussed. Display 620 may indicate various pieces of information to the user. In accordance with some embodiments, some or all of this information may also be conveyed to a healthcare professional and/or associated third party.

Display 620 may show a user's goal 621 for a particular activity. The activity itself may be identified or explained at 622. Display 620 may also include a graphical representation, in any format, of the amount of activities done or performed, compared with what is remaining. For example, FIG. 6 illustrates this graphical representation in the form of a dynamic pie graph that may slowly close to illustrate completion of the activity.

Figure 7:
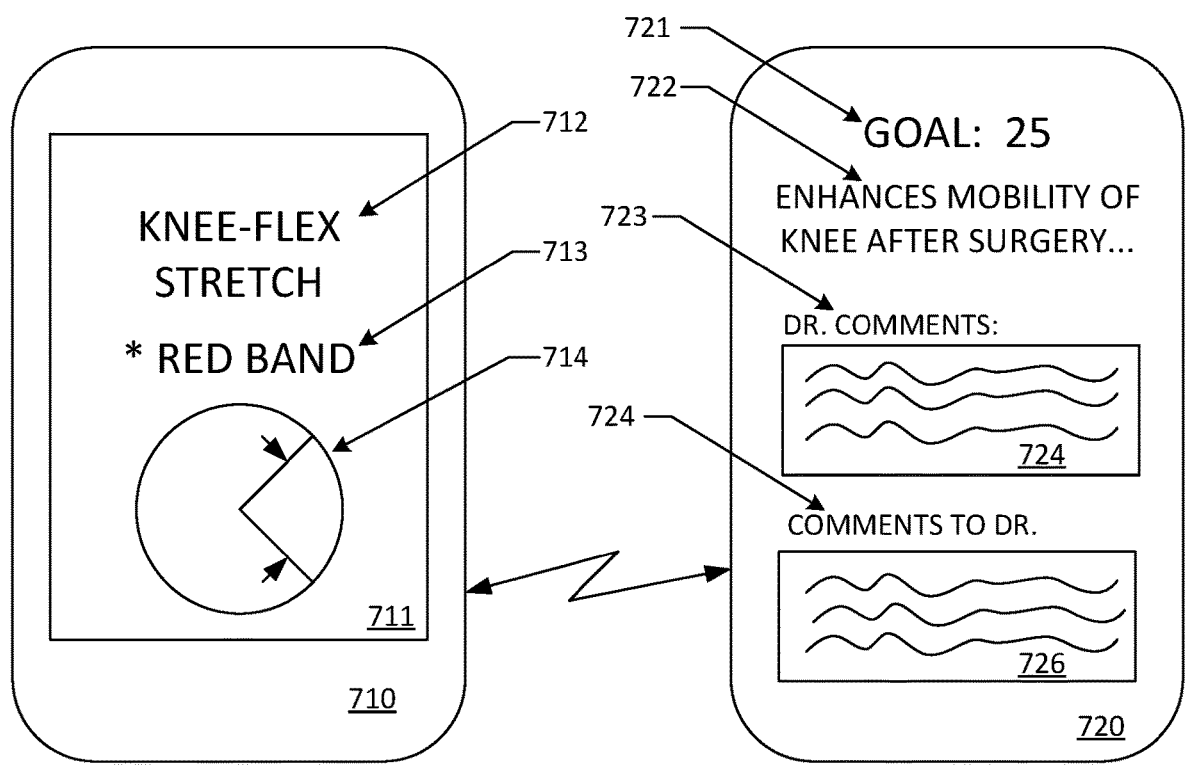
FIG. 7 depicts an exemplary system with illustrative displays for measuring force and/or repetitive motions, in accordance with some embodiments of the present invention.

With reference to FIG. 7, a display 711 on the measuring device 710 may shown in comparison to a display 720 on a communicatively linked user device. The device 710 may include a display 711 that may only show limited information, such as the type of exercise 712 ("KNEE-FLEX STRETCH"), what band should be used 713 ("RED BAND") or what valve setting may be used on a pneumatic device, and a graphical representation of progress 714.

In contrast to the limited information displayed on the device, the user's device (such as but not limited to a mobile telephone or smartphone) may show additional information. For example, the user's phone may display the goal at 721, the rationale or reason for the goal 722, an area for comments from a healthcare professional 723, which may include a field 724 editable by such professional (or a member of their office), as well as an area 725 for comments from the user that may include a field 726 editable by the user to provide communication back and forth with the healthcare professional.

Figure 8:
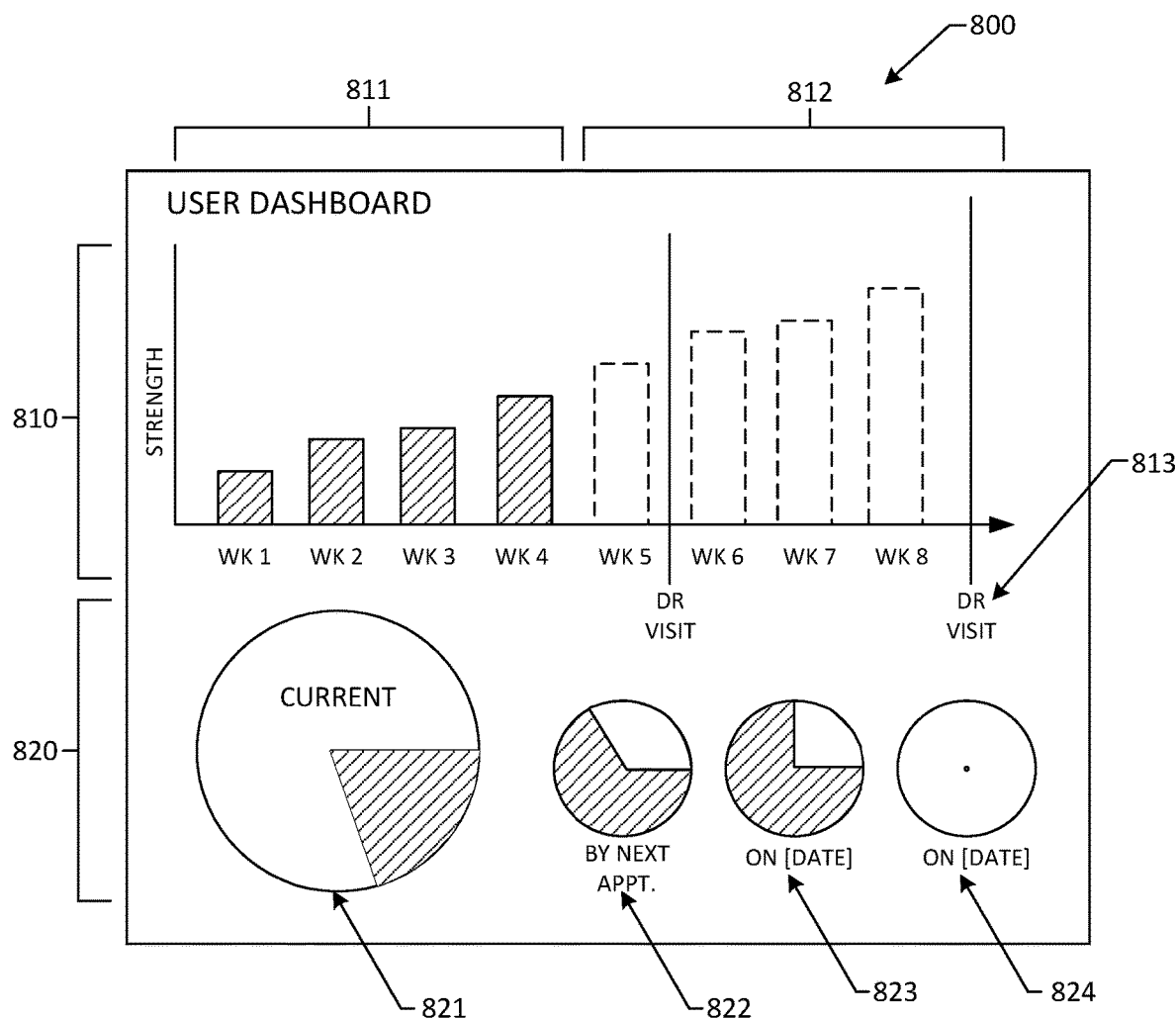
FIG. 8 depicts an exemplary user dashboard, which may be used in accordance with some embodiments of the present invention.

With reference to FIG. 8, a user dashboard 800 that may accessible through an app, or by accessing a data store or website will now be disclosed. Dashboard 800 may comprise multiple information, including for example, a graphical representation of user progress 810. This may comprise a chart 810 showing the user's progress 811, anticipated or progress goals 812, and may even indicate the timing of doctor or other healthcare visits 813. Dashboard 800 may also comprise other graphical representations 820 showing the current state of exercise/strength/flexibility/etc., what is anticipated by the next appointment 822, and other benchmarks 823, and an anticipated completion date 824.

FIG. 9 indicates a force curve of typically used exercise resistance bands, comparing force 910 to percent elongation 920 of the band. It can be seen, in this example, that the force of a yellow band 930 ranges from approximately 11 kg at 50% elongation to approximately 26 kg at 300% elongation. Similar information is shown for a red band 940, green band 950, blue band 960, and black band 970. The black band 970 may have a force resistance equal to approximately 27 kg at 50% elongation, but as much as 75 kg at 300% elongation. It can be seen from this information how difficult it may be for a user to understand how much force they are opposing, and how difficult it may be to assemble a cumulative fitness plan.

In light of the varying forces that may be associated with such resistance bands, FIG. 10 illustrates a display 1000 in accordance with some embodiments of the present invention. The display may be presented on either the device itself, or on a user-device, such a smart phone. The display 1000 may indicate the exercise in question 1010 ("BICEP CURLS"), general information about the exercise 1020, what band or pneumatic valve setting is recommended 1030, general timing issue or other advice at 1040, and a dynamic display that shows the amount of force currently applied by the user 1050, and the target force presented as a goal 1060. In this manner, if a user wants to curl thirty (30) kilograms, the user can know the precise moment they are pulling this weight, as opposed to merely knowing an approximate range of forces associated with a specific band or making a guess at a valve setting.

In the case of a bicep curl, a user may not be able to cause more elongation of the band or pneumatic device (as the motion associated with a curl is relatively limited). If the force falls short of the goal, then the display may indicate an alteration to achieve the goal. For example, at 1070 the display may note to "SHORTEN BAND" or "CLOSE VALVE ½ TURN" By shortening the band, the range of motion of the bicep curl will be a greater degree of elongation from the original length, thereby increasing the force and (hopefully) achieving the desired goal. By closing the valve, increased force may be required to push or pull the piston through the cylinder.

Figure 11:
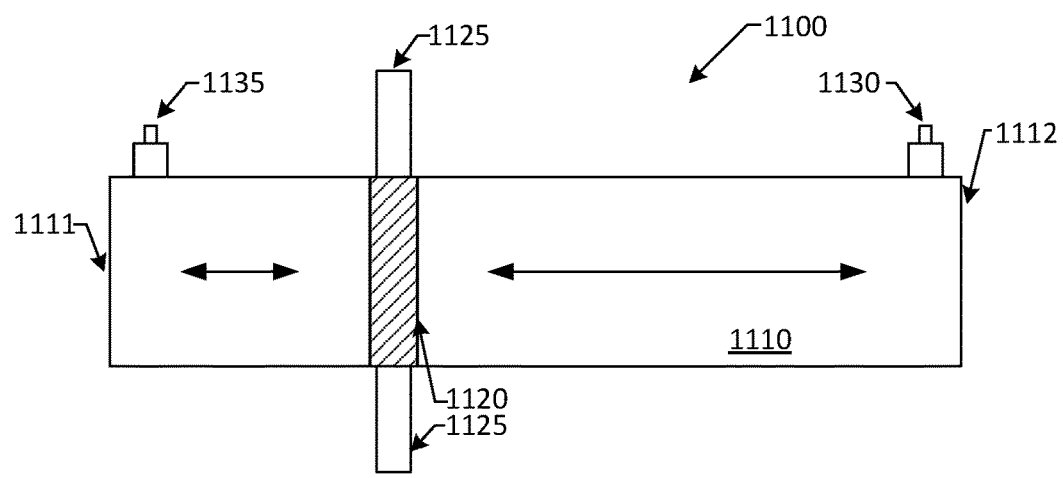
FIG. 11 illustrates an exemplary pneumatic exercise device, in accordance with some embodiments of the present invention.

With reference to FIG. 11, a pneumatic device 1100 will now be discussed. Pneumatic device 1100 may generally comprise a cylinder or open vessel 1110, with a piston 1120 disposed therein. Piston 1120 may be moved by a user from a first end 1111 to a second end 1112 of the cylinder 1110. As piston 1120 moves from first end 1111 to second end 1112 and back, it may compress air or another fluid (e.g., a liquid) in cylinder 1110. Valves 1130 and 1135 may be used to control the rate of the release and reentry of fluid into the cylinder 1110, thereby impacting the force applied by the user to effectuate such actions. Exemplary devices as discussed above may be attached to piston 1120—for example, at attachment 1125.

The device may be attached between a handle, bar, strap, or other device that may be held, pulled, pushed, or grasped by a user and the piston 1120.

Figure 12:
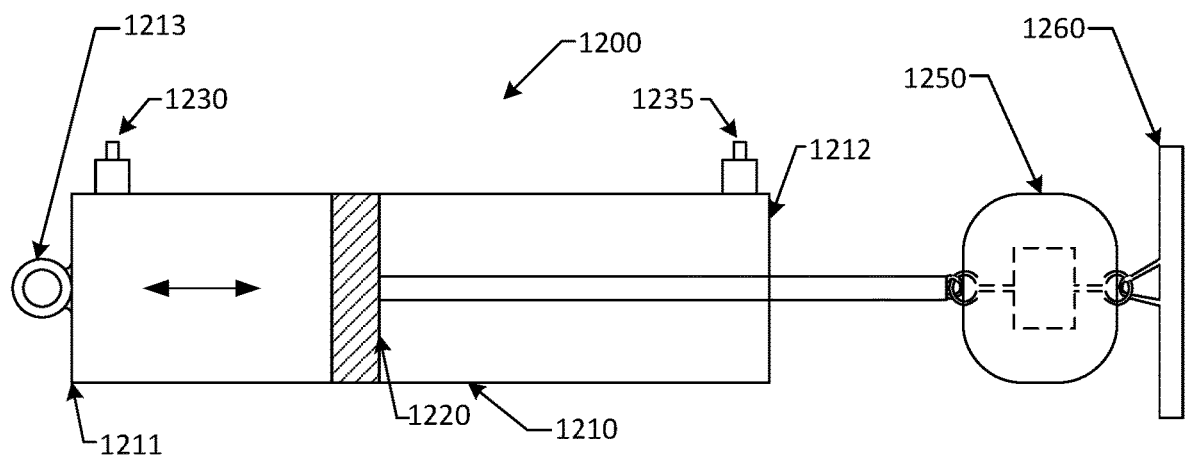
FIG. 12 illustrates an exemplary pneumatic exercise device, in accordance with some embodiments of the present invention.

With reference to FIG. 12, a pneumatic exercise device 1200 in accordance with some embodiments will not be discussed. Pneumatic exercise device 1200 may generally comprise a cylinder 1210, with a piston 1220 disposed therein. Cylinder 1210 may comprise a first end 1211 and a second end 1212. One end of the cylinder 1210 may include a mount or attachment device 1213 for connecting the pneumatic exercise device 1200 to a support or other equipment (not shown). Pneumatic exercise device 1200 may further comprise a valve 1230, 1240 which may permit the flow of air or other fluid from an ambient environment into or out of the cylinder. Valves 1230, 1240 may be adjusted by a user to control the rate of release of air or other fluid, or to require a certain degree of compression or vacuum before the valves 1230, 1240 permit fluid flow therethrough.

The piston 1220 may be attached to a pushrod 1225, which may extend out of the cylinder 1220, and may be attached to a device 1250 for tracking repetitions and/or determining forces actually applied by a user. Device 1250 may be attached to a handle, strap, bar, or other element 1260 that may be held, pushed, pulled, or grasped by a user.

In operation, a user may push or pull on handle, bar, strap, or other device 1260, thereby causing a force to be applied to piston 1220 by way of pushrod 1225. As the piston 1220 slides from one end of the cylinder 1210 to the other, the movement may cause a compression in the volume being reduced, while causing a vacuum in the volume being increased. Air or other fluid in the compression side may exit the cylinder 1210 via valve 1230 or 1240, while air or other fluid in the vacuum side my enter the cylinder 1210 via the other valve 1230, 1240.

Note it is contemplated that one valve may be replaced with a direct opening, permitting fluid flow directly into cylinder 1210 without any additional force required. In this embodiment, the device would be a single-action pneumatic cylinder, in that significant force would be required by a user for only direction of movement of the piston 1220. It is contemplated that the present invention may be used with single-action or double-action pneumatic cylinders.

Figure 13:
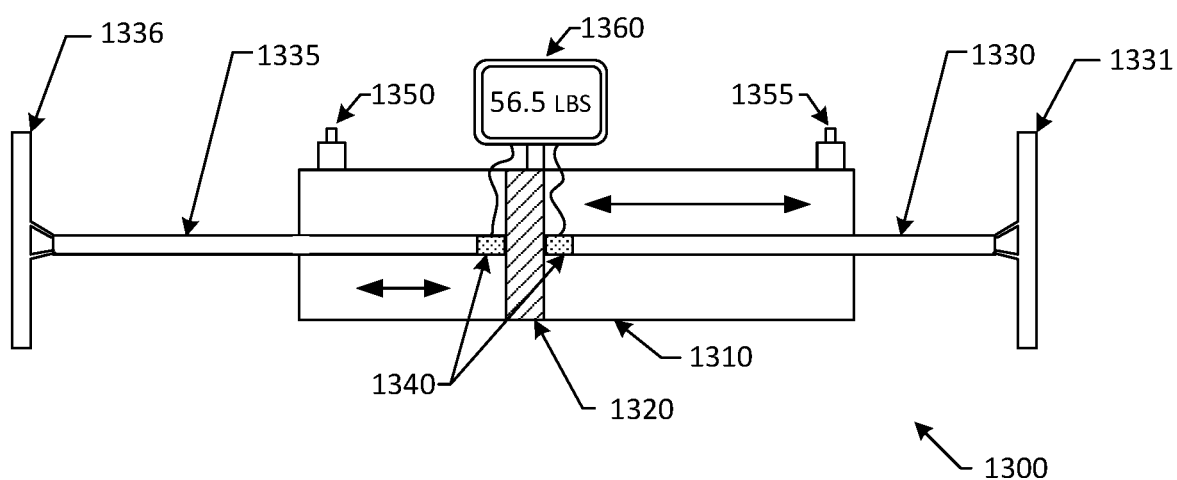
FIG. 13 illustrates an exemplary pneumatic exercise device, in accordance with some embodiments of the present invention.

With reference to FIG. 13, an exemplary double-action pneumatic exercise device 1300 will now be discussed. Double-action pneumatic exercise device 1300 may again generally comprise a cylinder 1310 with a piston 1320 disposed therein. Piston 1320 may be connected to two pushrods 1330, 1335, which may in turn be connected to a handle, bar, strap, or other element that may be pushed, pulled, or grasped by a user, or attached to a fixture, mount, or other device. Cylinder 1310 may again comprise valves 1350, 1355 to control and/or limit the flow of air or other fluid into and out of the cylinder 1310. Double action pneumatic exercise device 1300 may further comprise one or more force sensors 1340, which may be connected to a visual display 1360. Force sensors 1340 may determine the amount of force applied by the user through pushrods 1330, 1335, applied to the piston 1320, and may display the same to a user. As noted above, such device may have various wired and/or wireless connectivity, may track repetitions, routines, etc., and may report the same to various medical and/or athletic service providers.

It will be understood that the specific embodiments of the present invention shown and described herein are exemplary only. Numerous variations, changes, substitutions and equivalents will now occur to those skilled in the art without departing from the spirit and scope of the invention. For example, while the device as shown shows fluid entering and exiting a cylinder from and to an ambient environment, it is also contemplated that a valve may be placed on a piston itself, to control the conveyance of fluid from one side of the piston to the other, thereby providing a closed-circuit device. Such a device may utilize a gas (pneumatic) that may be compressed or may utilize a noncompressible fluid (hydraulic) to effectuate different resistance settings. Accordingly, it is intended that all subject matter described herein and shown in the accompanying drawings be regarded as illustrative only, and not in a limiting sense.

What is claimed is:

1. An exercise and/or therapeutic device that measures force and repetitions during exercise or rehabilitation activities, the device comprising:
   a measuring device, comprising:
      a casing;
      a processor disposed within the casing;
      a display visibly disposed on the casing and communicatively connected to the processor;
      a first attachment portion on one end of the casing;
      a second attachment portion on an opposite end of the casing from the first attachment portion; and
      a force sensor disposed within the casing and connected to the first attachment portion and the second attachment portion, the force sensor in communication with the processor;
   a pneumatic exercise device comprising a piston disposed in a cylinder, the cylinder having at least one valve to control flow of air into and out of the cylinder;
   wherein the measuring device measures the force applied to the piston in both directions of travel through the cylinder.

2. The measuring device of claim 1, further comprising a memory unit within the casing and in communication with the processor.

3. The measuring device of claim 1, further comprising a communication module.

4. The measuring device of claim 3, wherein the communication module comprises a port to receive a wired connection to a user device.

5. The measuring device of claim 3, wherein the communication module comprises wireless communication capability.

6. The measuring device of claim 5, wherein the wireless communication module is over a WiFi network.

7. The measuring device of claim 5, wherein the wireless communication module communicates with a remote computing device via direct cellular communications.

8. A method for measuring force and repetitions during exercise or rehabilitation activities, using a wireless force measurement device, the method comprising:
   attaching a pneumatic exercise device to the wireless force measurement device, the pneumatic exercise device comprising a piston disposed in a cylinder, the cylinder having at least one valve to control flow of air into and out of the cylinder;
   conducting exercises causing the piston to push or pull away from the wireless force measurement device;
   counting, by the wireless force measurement device, the number of times the piston moves away from the wireless force measurement device;
   determining, by the wireless force measurement device the amount of force applied through the pneumatic exercise device in both directions of travel through the cylinder during the exercise.

9. The method of claim 8, further comprising:
   displaying to a user the number of times the piston moves away from the wireless force measuring device or the amount of force applied through the pneumatic exercise device during the exercise.

10. The method of claim 8, further comprising:
    communicating to a remote device the number of times the piston moves away from the wireless force measuring device or the amount of force applied through the pneumatic exercise device during the exercise.

11. The method of claim 10, wherein the remote device is disposed at an office of a health care professional.

12. The method of claim 10, wherein the remote device is a computing or mobile device of a user.

* * * * *